United States Patent
Ruimi et al.

(12) 
(10) Patent No.: US 6,582,585 B2
(45) Date of Patent: Jun. 24, 2003

(54) METHOD OF REVEALING STRUCTURE FOR SINGLE-CRYSTAL SUPERALLOYS

(75) Inventors: Michel Ruimi, Paris (FR); Sylvie Poutonnet, Vaux le Penil (FR); Philippe Poubanne, Vigneux sur Seine (FR)

(73) Assignee: SNECMA Moteurs, Paris (FR)

( * ) Notice: Subject to any disclaimer, the term of this patent is extended or adjusted under 35 U.S.C. 154(b) by 0 days.

(21) Appl. No.: 09/938,495

(22) Filed: Aug. 27, 2001

(65) Prior Publication Data

US 2002/0023846 A1 Feb. 28, 2002

(30) Foreign Application Priority Data

Aug. 28, 2000 (FR) .............................. 00 10979

(51) Int. Cl.$^7$ ................................. C25F 3/00
(52) U.S. Cl. ...................... 205/682; 205/653; 205/660; 205/680
(58) Field of Search ................. 205/660, 674, 205/680, 652, 653, 682, 646

(56) References Cited

U.S. PATENT DOCUMENTS

| 4,234,397 A | * 11/1980 | Torrey ........................ 205/661 |
| 4,445,988 A | 5/1984 | Steeves et al. ........... 204/129.2 |
| 4,548,903 A | 10/1985 | Weiss et al. ................... 436/5 |
| 4,801,367 A | * 1/1989 | Burgess et al. ........ 204/224 M |

FOREIGN PATENT DOCUMENTS

| EP | 0 971 041 | 1/2000 |
| WO | WO 93/04370 | 3/1993 |
| WO | WO 98/20341 | 5/1998 |

* cited by examiner

*Primary Examiner*—Patrick Ryan
*Assistant Examiner*—Thomas H. Parsons
(74) *Attorney, Agent, or Firm*—Oblon, Spivak, McClelland, Maier & Neustadt, P.C.

(57) ABSTRACT

The method according to the invention comprises a macrographic etching step followed by a "bleaching" step by electrolytic etching by means of a bath containing at least phosphoric acid and a weak acid. This method allows components made of superalloys to be easily and effectively inspected, including when they contain elements such as rhenium or ruthenium.

20 Claims, 1 Drawing Sheet

METHOD OF REVEALING STRUCTURE FOR SINGLE-CRYSTAL SUPERALLOYS

BACKGROUND OF THE INVENTION

It is well known to use refractory metal alloys, particularly single-crystal superalloys, to produce components designed to be exposed, in service, to high temperatures. This is thus the case particularly with gas turbine components, such as fixed or moving blades of turbojets.

Components made of a single-crystal superalloy, such as the aforementioned blades, are manufactured by casting, with control of the solidification process.

Inspection of the just-cast components is necessary in order to detect possible defects, such as inclusions, cracks or crazes, which are liable to affect their mechanical behaviour in service.

For this purpose, it is known to carry out macrographic etching of the surface of the components by means of an acid bath. One bath commonly used is a bath containing chloride ions, particularly a bath containing hydrochloric acid and iron perchloride in aqueous solution.

The Applicant has found that the treatment using this bath loses its effectiveness with certain types of superalloys, particularly nickel-based superalloys containing elements such as rhenium or ruthenium. However, the use of these types of superalloys may prove to be necessary in order to allow ever higher service temperatures allowing the efficiency of turbojets to be increased.

SUBJECT AND SUMMARY OF THE INVENTION

It is an object of the invention to provide a method of revealing structure which allows components made of superalloys to be easily and effectively inspected, including when they contain elements such as rhenium or ruthenium.

This object is achieved by means of a method which comprises a macrographic etching step followed, according to the invention, by a "bleaching" step by electrolytic etching by means of a bath containing at least phosphoric acid and a weak acid.

The weak acid is, for example, chosen from acetic acid, tartaric acid and citric acid.

Combining phosphoric acid with a weak acid makes it possible to compensate for the selective effect of the etching by the phosphoric acid with respect to certain constituents of the superalloy, a weak acid, such as acetic acid or the like, acting on other constituents, in particular nickel, which is a standard basic constituent of superalloys.

The bath may furthermore contain a constituent capable of making the rate of dissolution during electro-chemical etching uniform, for example a secondary alcohol such as glycol.

According to one particular aspect of the invention, the prior macrographic etching step is advantageously carried out chemically by means of a conventional acid bath containing chloride ions and iron perchloride. Such prior etching of superalloys, especially those containing rhenium and/or ruthenium, causes the component to be blackened because of the persistent formation of rhenium oxide and/or ruthenium oxide on the surface. The electrochemical etching then carried out in accordance with the invention allows the surface to be bleached or cleaned by the removal of these oxides. A visual inspection of the component can then be easily made. Carrying out these two—chemical and electrochemical—etching operations, one after the other, makes it possible to combine the effectiveness of each of the baths used with respect to the various elements of the superalloy.

Use of the electrochemical technique allows the reactivity, especially with respect to nickel-based alloys enriched with elements such as Re and Ru, to be increased. The superalloy component is immersed in the bath and arranged so as to be the anode facing a specific cathode having a shape suitable for obtaining a uniform distribution of the lines of current onto the component.

BRIEF DESCRIPTION OF THE DRAWINGS

The invention will be more clearly understood on reading the description below, given by way of indication but implying no limitation, in which reference will be made to the appended drawings in which.

DETAILED DESCRIPTION OF WAYS OF IMPLEMENTING THE INVENTION

Figure 1:
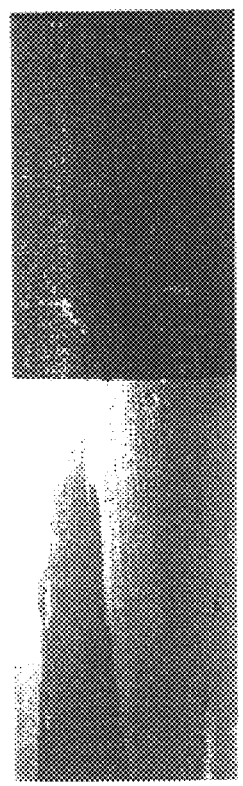
FIG. 1 is a photograph showing the effectiveness of the method according to the invention for bleaching the surface of a component made of a single-crystal superalloy for the purpose of visually inspecting it.

The invention is more particularly applicable to revealing the structure of components made of single-crystal superalloys containing rhenium and/or ruthenium.

Nickel-based single-crystal superalloys of this type, intended more particularly for the production of turbojet blades, are described, for example, in the document FR 98/08693. Their composition by weight is: 3.5 to 7.5% Cr, 0 to 1.5% Mo, 1.5 to 5.5% Re, 0 to 5.5% Ru, 3.5 to 8.5% W, 5 to 6.5% Al, 0 to 2.5% Ti, 4.5 to 9% Ta, 0.08 to 0.12% Hf, 0.08 to 0.12% Si, the balance being nickel or possible impurities. Of course, the field of application of the invention is not limited to alloys meeting this particular definition.

According to one particular way of implementing the invention, a method of revealing structure for a component made of a single-crystal superalloy comprises the steps consisting in:

subjecting the component to a first, chemical macrographic etching operation by means of a first acid bath containing, conventionally, chloride ions;

rinsing the component;

drying the component with compressed air;

subjecting the component to a second etching operation using an electrochemical technique by means of a second acid bath containing, in accordance with the invention, phosphoric acid and at least one weak acid;

rinsing the component; and optionally, drying the component, which can be visually inspected in order to detect possible manufacturing defects.

The first, chemical etching operation may be carried out using a bath containing hydrochloric acid and iron perchloride dissolved in water. The proportions by weight of hydrochloric acid and iron perchloride are, for example, between 70 and 80% and between 5 and 10%, respectively, the balance being water.

The etching is carried out by immersing the component in the bath at a temperature of approximately 50° C. to 70° C. for a time of between 15 min and 30 min. Of course, several components may be treated concomitantly.

After rinsing the component with deionized water, the second etching operation, using an electrochemical technique, is carried out using the bath containing phosphoric acid and at least one weak acid. Advantageously, the latter is chosen from acetic acid, tartaric acid and citric acid. An additional constituent, whose purpose is to soften the chemical etching, may be added. For this purpose, a secondary alcohol may be used.

As an example, the proportions by volume of the various constituents of the bath may be the following: 30 to 80% phosphoric acid, 3 to 15% weak acid, such as acetic acid, and 0 to 15% secondary alcohol, such as glycol, the balance being water.

The component immersed in the bath is connected to an anode and is surrounded by a cathode. The shape of the cathode is chosen according to that of the component, in order to ensure the most uniform distribution of the lines of current (equipotentials) in the bath and, consequently, the lines of current onto the component itself, so as to treat the latter in an approximately uniform manner. The anode current density is relatively high, for example between 10 and 60 A/dm$^2$. The duration of the electrochemical etching may be relatively short, for example between 1 min and 5 min.

EXAMPLE 1

A bar of a nickel-based single-crystal superalloy, of the type defined in the aforementioned document FR 98/08693, containing rhenium and ruthenium, was treated in the following manner.

- first chemical macrographic etching in an acid bath containing, by weight, 77% hydrochloric acid, 7% iron perchloride and 16% water at a temperature of 55° C. for 20 min.;
- rinsing with deionized water;
- drying with compressed air;
- second etching using an electrochemical technique carried out on part of the bar immersed in an acid bath containing, by volume, approximately 60% phosphoric acid, approximately 10% acetic acid and approximately 5% glycol, the balance being water; the immersed part of the bar was connected up as the anode phase and surrounded by a cylindrical cathode made of stainless steel sheet; the chemical etching was carried out for 2 min.;
- rinsing with distilled water; and
- drying in a stream of warm air.

FIG. 1 shows the bar obtained, in its upper part, after the first, chemical etching operation and, in its lower part, after the second, electrochemical etching operation.

The surface of the upper part is blackened by the presence of rhenium and ruthenium oxides, making visual inspection difficult, if not impossible.

The surface of the lower part, cleaned ("bleached") by the second, electrochemical etching operation, clearly reveals possible manufacturing defects (in particular, in the photograph in FIG. 1, the presence of an inclusion of darker color).

EXAMPLE 2

Just-cast blades, made of a nickel-based single-crystal superalloy, of the type defined in the aforementioned document FR 98/08693, containing 4% rhenium and 4% ruthenium, were treated in the manner described in Example 1 except for the fact that they were entirely subjected to the second, electrochemical etching operation, by being completely immersed in the acid bath.

Figure 2:
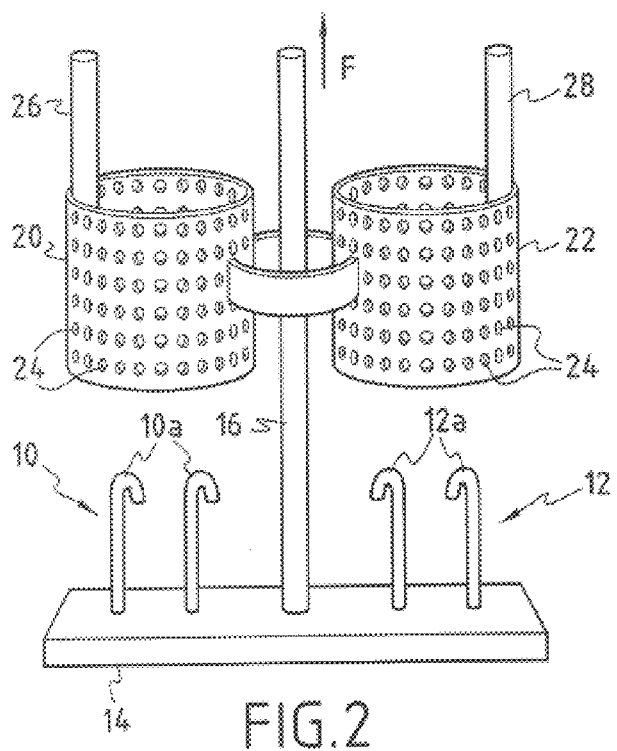
FIG. 2 shows an illustrative example of an arrangement for implementing a method according to the invention.

The arrangement shown in FIG. 2 was used, allowing the two blades to be treated at the same time. This arrangement, placed in a tank, comprised two anodes 10, 12 mounted on a common support 14 connected by a bar 16 to an external supply terminal (not shown), the assembly being made of stainless steel. The anodes were in the form of rods having, at their free end, a curved part 10a, 12a elastically deformable by pinching.

Associated with each component was a cathode, 20, 22 respectively. The cathodes had an approximately cylindrical shape. They were made of stainless steel and had a number of holes 24 through their wall. The cathodes were connected together and mounted at the ends of two bars 26, 28, also made of stainless steel. The bars 26, 28 were connected to an external supply terminal (not shown).

The bar 16 could slide (arrow F) so as to bring the anodes into a position in which they were surrounded by the cathodes.

Figure 3:
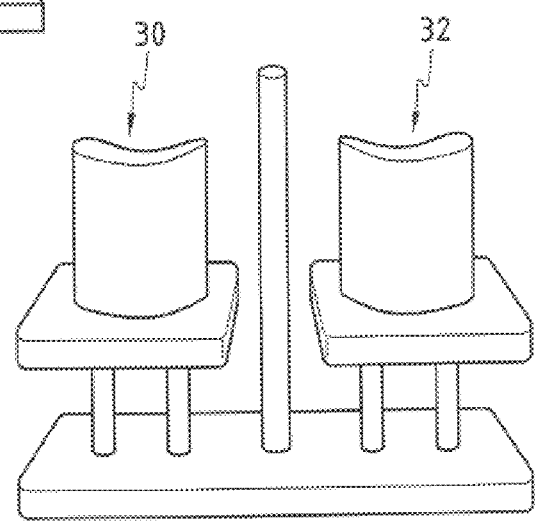
FIG. 3 shows blades connected up as anodes in the arrangement in FIG. 2.

FIG. 3 shows partially the arrangement in FIG. 2 with two blades 30, 32 mounted on the anodes. The blades were supported and electrical contact with them was made by fitting the anodes, and by pinching their curved ends, in internal channels of the blades. Of course, different forms of arrangements could be used, depending on the shapes and possibilities afforded by the components to be treated.

After mounting the blades, the cathodes were put into position around them and the assembly was immersed in the acid bath. The dimensions and shape of the cathodes were specifically chosen so that they surrounded the blades so as to leave a relatively constant gap, for example of about 30 mm, between them. Good distribution of the lines of current in the bath could thus be obtained, allowing the surface of the blades to be treated relatively uniformly.

The holes 24 in the cathodes favour the evolution of gas (O$_2$) which takes place and limit the heat-up of the bath by the Joule effect by avoiding a confinement of the space between the facing anode and cathode.

The electrochemical etching operation was carried out under the conditions in Example 1, with an anode current density of approximately 30 A/dm$^2$. After electrochemical etching for 2 mins, the blades were removed from the bath, rinsed and dried. They had a light-coloured external surface, allowing any manufacturing defects to be easily seen.

The arrangement described above allows two components to be treated simultaneously. Of course, similar arrangements may be used for treating a single component or, simultaneously, a number of components greater than two.

What is claimed is:

1. A method for revealing a structure of a component made of a single-crystal superalloy, comprising:
   - subjecting the component to a chemical macrographic etching; and
   - subjecting the component subjected to the chemical macrographic etching to an electrochemical etching in a bath containing phosphoric acid and at least one weak acid.

2. The method according to claim 1, wherein the at least one weak acid is selected from the group consisting of acetic acid, tartaric acid and citric acid.

3. The method according to claim 1, wherein the bath further contains a secondary alcohol.

4. The method according to claim 3, wherein the secondary alcohol is glycol.

5. The method according to of claim 1, wherein the bath contains, by volume, 30 to 80% phosphoric acid, 3 to 15% weak acid and 0 to 15% of a secondary alcohol.

6. The method according to claim 1, wherein the electrochemical etching comprises immersing the component in the bath, connecting the component as an anode and surrounding the component by a cathode.

7. The method according to claim 6, wherein the cathode has a shape tailored to the component so as to leave between the cathode and component an approximately uniform gap.

8. The method according to claim 7, wherein the cathode has holes.

9. The method according to claim 1, wherein the electrochemical etching is carried out for between 1 mm and 5 mm.

10. The method according to claim 1, wherein the chemical macrographic etching is carried out by immersing the component in a bath containing chloride ions and iron perchloride.

11. A method for revealing a structure of a turbojet engine blade made of a single-crystal superalloy containing at least one of rhenium and ruthenium, the method comprising:

etching at least a portion of the turbojet engine blade using a chemical macrographic etching etching process; and electrochemically etching at least a part of the etched portion of the turbojet engine blade in a bath containing phosphoric acid and at least one weak acid.

12. The method according to claim 11, wherein the at least one weak acid is selected from the group consisting of acetic acid, tartaric acid and citric acid.

13. The method according to claim 11, wherein the bath further contains a secondary alcohol.

14. The method according to claim 13, wherein the secondary alcohol is glycol.

15. The method according to of claim 11, wherein the bath contains, by volume, 30 to 80% phosphoric acid, 3 to 15% weak acid and 0 to 15% of a secondary alcohol.

16. The method according to claim 11, wherein the electrochemically etching at least a part of the etched portion of the turbojet engine blade comprises immersing the part of the etched portion of the turbojet engine blade in the bath, connecting the turbojet engine blade as an anode and surrounding the immersed part of the etched portion of the turbojet engine blade with a cathode.

17. The method according to claim 16, wherein the cathode is shaped so as to provide an approximately uniform gap between the cathode and the immersed part of the etched portion of the turbojet engine blade surrounded by the cathode.

18. The method according to claim 17, wherein the cathode has holes.

19. The method according to claim 11, wherein the electrochemical etching is carried out for between 1 min and 5 min.

20. The method according to claim 11, wherein the chemical macrographic etching process comprises immersing at least a portion of the turbojet engine blade in a bath containing chloride ions and iron perchloride.

* * * * *